(12) United States Patent
Khalaj

(10) Patent No.: US 9,901,728 B2
(45) Date of Patent: Feb. 27, 2018

(54) CATHETER CONNECTOR INSERT

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

(*) Notice: Subject to any disclaimer, the term of this patent is extended or adjusted under 35 U.S.C. 154(b) by 854 days.

(21) Appl. No.: 14/279,969

(22) Filed: May 16, 2014

(65) Prior Publication Data

US 2015/0328445 A1    Nov. 19, 2015

(51) Int. Cl.
*A61M 39/10* (2006.01)
*A61M 39/06* (2006.01)
*A61M 39/20* (2006.01)
*A61M 25/00* (2006.01)

(52) U.S. Cl.
CPC .... *A61M 39/1011* (2013.01); *A61M 25/0097* (2013.01); *A61M 39/06* (2013.01); *A61M 39/20* (2013.01); *A61M 2039/062* (2013.01)

(58) Field of Classification Search
CPC .. A61M 39/10; A61M 39/1011; A61M 39/20; A61M 2039/1027; A61M 2039/1033; A61M 2039/1038; A61M 2039/1066; A61M 5/002; A61M 5/31571; A61M 25/002; A61M 2205/27; A61M 2205/276; A61B 50/30; B65D 25/106
See application file for complete search history.

(56) References Cited

U.S. PATENT DOCUMENTS

| 4,248,236 A | 2/1981 | Linder |
| 5,147,336 A | 9/1992 | Wendell et al. |
| 5,464,400 A | 11/1995 | Collins |
| 8,611,993 B2 | 12/2013 | Vitullo et al. |
| 2012/0000254 A1 | 1/2012 | Zhao |
| 2014/0303595 A1* | 10/2014 | Justus ................ A61M 5/5086 604/508 |
| 2015/0290449 A1* | 10/2015 | Yanik ................ A61M 39/1011 604/533 |
| 2015/0369402 A1* | 12/2015 | Pa ........................ F16L 49/06 285/386 |

FOREIGN PATENT DOCUMENTS

EP    0 046 464 A1    3/1982

OTHER PUBLICATIONS

PCT Search Report, dated Aug. 3, 2015.

* cited by examiner

*Primary Examiner* — Kami A Bosworth
(74) *Attorney, Agent, or Firm* — Dority & Manning, P.A.

(57) ABSTRACT

The present invention relates to a catheter connector assembly having an insert for use during packaging, shipping, and handling of a catheter connector. The assembly includes a catheter connector having a body with a first half axially aligned with a second half. The first half is rotatable relative to the second half between an open position and a closed position. The first half defines a distal end of the body and the second half defines a proximal end of the body. A proximal end port is configured with the proximal end of the second half for mating communication with a fluid delivery device. The insert is configured with the body when the body is in the open position such that the insert maintains the catheter connector in the open position during packaging, shipping, and handling of the catheter connector.

5 Claims, 3 Drawing Sheets

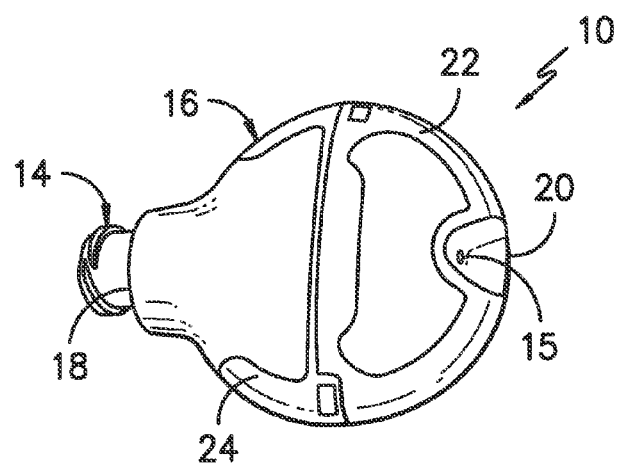
FIG. -1-
(PRIOR ART)
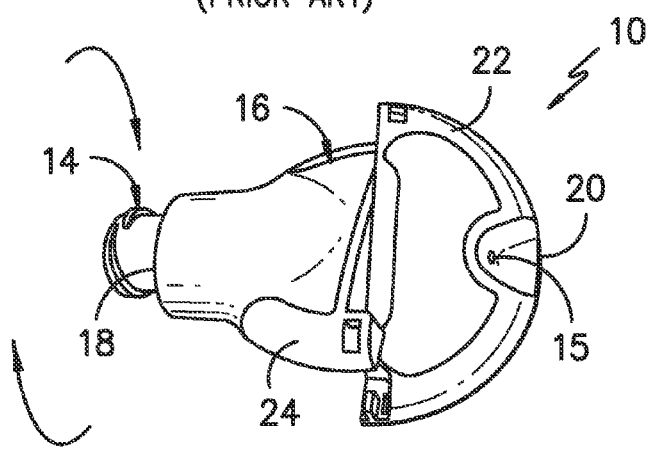
FIG. -2-
(PRIOR ART)
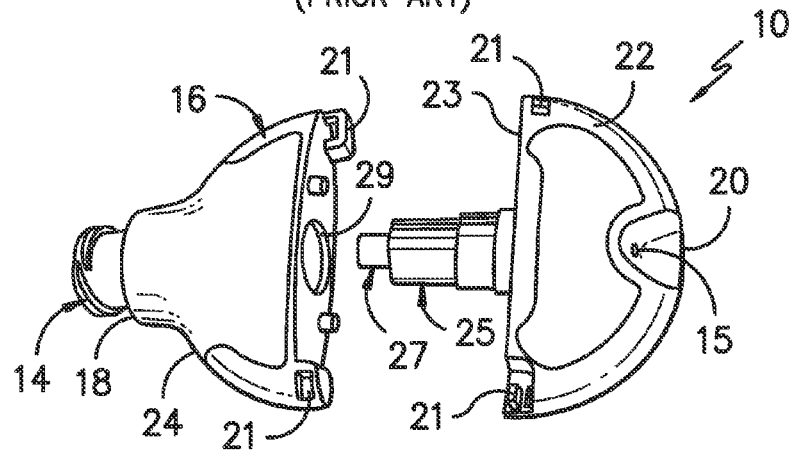
FIG. -3-
(PRIOR ART)

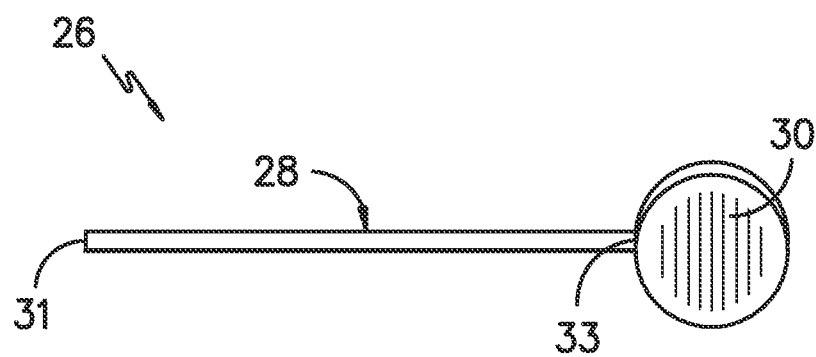
FIG. -4-
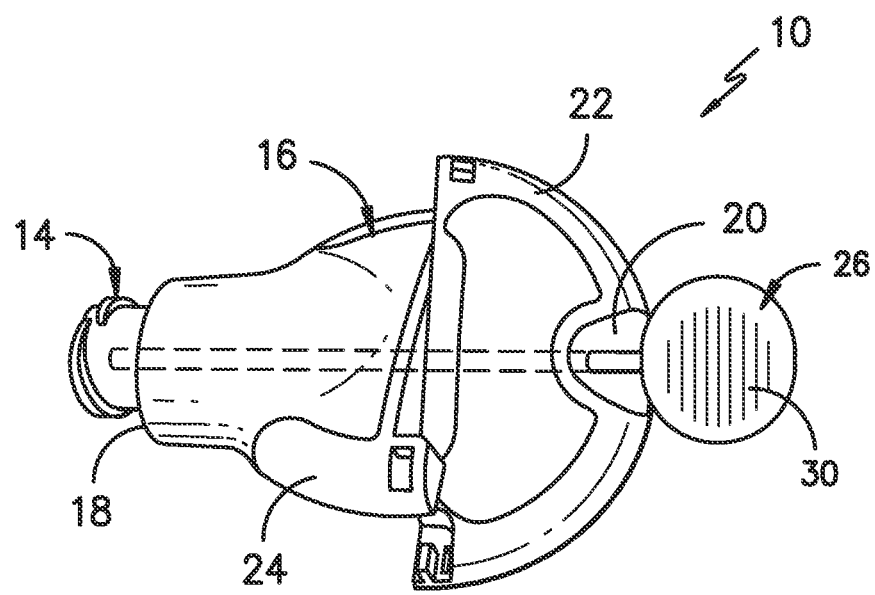
FIG. -5-

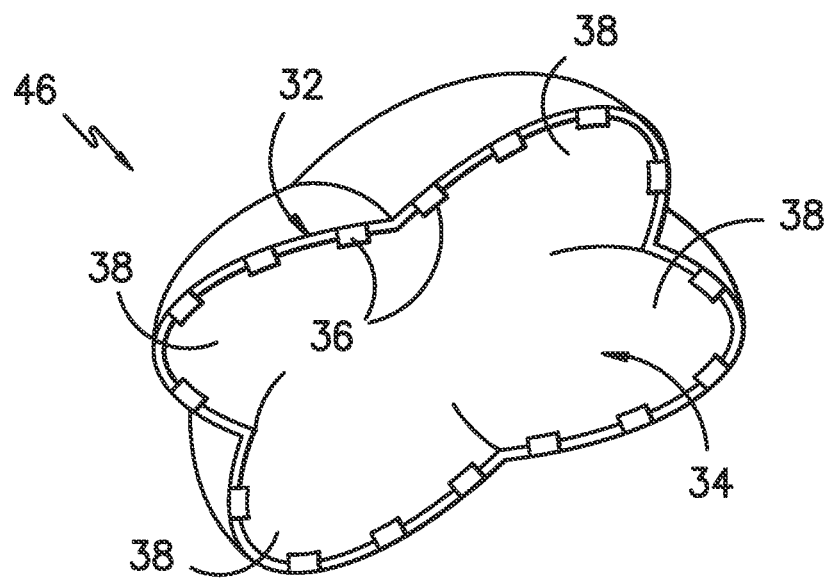
FIG. -6-
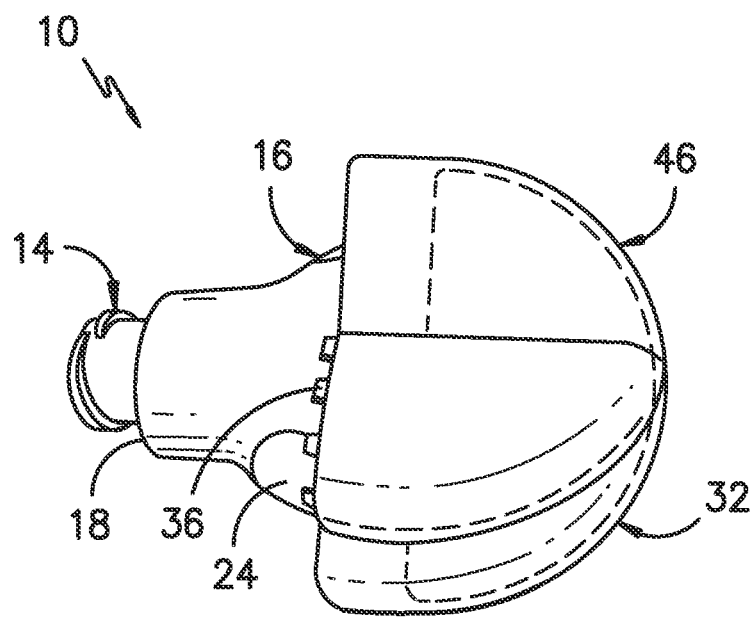
FIG. -7-

CATHETER CONNECTOR INSERT

FIELD OF THE INVENTION

The present invention relates generally to the field of medical catheters and more particularly to inserts for catheter connectors for using during packaging, shipping, and handling.

BACKGROUND

The use of catheters to deliver or withdraw fluids from a patient for various medical procedures is well known. For example, U.S. Pat. No. 7,959,623 describes a pain management system that uses various embodiments of infusion catheters to deliver fluid medication from a pump, through tubing, to a wound site. With such configurations, catheter connectors are typically used to connect the catheter to various devices, such as tubing, a fluid reservoir or other fluid delivery device, and so forth. In the system of the '623 patent, a conventional Tuohy-Borst connector is used to connect the distal end of a medical tube to the proximal end of the catheter.

In addition to Tuohy-Borst connectors, various other configurations of catheter connectors are available. For example, Epimed International of Farmers Branch, Tex., U.S.A., manufactures a low profile twist-lock catheter connector known as the "Stingray™" connector. This device has axially aligned halves that twist to an open position to allow insertion of the catheter in a first half, and subsequently twist to a closed position with an audible and tactile click that indicates complete engagement with the catheter. The second half connects to a tube or other fluid delivery device for delivering fluid through the connector to the catheter. Further, between the two halves is a molded bushing that includes an inner elastomeric tube that compresses and grips the catheter when the connector is in a closed position.

During packaging, shipping, and handling of the Stingray™ connector, as well as other connectors having a similar configuration, it is important for the connector to remain in an open position because, if the connector closes, the locking jaws will stay in the closed position and will not allow the catheter to be inserted therethrough. More specifically, when the connector is in a closed position, the two halves push inward to squeeze the inner elastomeric tube over the catheter. Since, the connector is typically made of a soft plastic, the molded bushing and inner elastomeric tube can lose their strength when in the closed position. As such, even when the load is removed, the inner diameter of the elastomeric tube may be smaller, which can inhibit the catheter from being inserted easily therethrough.

Accordingly, an insert designed to keep a catheter connector, such as a Stingray™ connector, in the open position during packaging, shipping, and handling would be welcomed in the art.

SUMMARY OF THE INVENTION

Objects and advantages of the invention will be set forth in part in the following description, or may be obvious from the description, or may be learned through practice of the invention.

In certain aspects, the present invention relates to a catheter connector assembly for use during packaging, shipping, and handling of a catheter connector. The assembly includes a catheter connector having a body with a first half axially aligned with a second half. The first half is rotatable relative to the second half between an open position and a closed position. The first half defines a distal end of the body and the second half defines a proximal end of the body. A proximal end port is configured with the proximal end of the second half for mating communication with a fluid delivery device. An insert is configured with the body when the body is in the open position such that the insert maintains the catheter connector in the open position during packaging, shipping, and handling of the catheter connector.

In one embodiment, the insert is configured to fit within the first and second halves of the body when the first half is in the open position such that the insert maintains the catheter connector in the open position. More specifically, in a particular embodiment, the insert may include a rod-shaped member configured to fit within the first and second halves when the first half is in the open position such that the insert maintains the catheter connector in the open position. In addition, the insert may also include a tab member configured with the rod-shaped member. The tab member is configured to extend outside of the catheter connector when the rod-shaped member is inserted within the first and second halves of the body. As such, the tab member is configured to assist a user with removing the insert from the catheter connector. In additional embodiments, the open position is defined by the first half being rotated relative to the second half at an approximately 45-degree angle.

In another embodiment, the insert may be configured to fit at least partially around an exterior surface of the body of the connector when the body is in the open position such that the insert maintains the catheter connector in the open position. More specifically, in a particular embodiment, the insert may further include a housing having a hollow interior. The hollow interior has a shape that corresponds to an exterior shape of the catheter connector in the open position. Thus, at least a portion of the catheter connector is configured to fit within the housing of the insert when the catheter connector is in the open position such the insert maintains the catheter connector in the open position during packaging, shipping, and handling.

In such an embodiment, the insert may also include one or more locking features configured to secure the insert at least partially around the exterior surface of the connector. For example, in various embodiments, the locking features may include at least one of or a combination of the following: molded snaps, add-on grips, ridges, protrusions, an adhesive, or similar.

In additional embodiments, the insert may be constructed of a rigid material. In various embodiments, the rigid material includes at least one of or a combination of the following: a plastic material, polycarbonate, polypropylene, polyurethane, polyester, epoxy resins, phenolic resins, polyvinyl chloride (PVC), a metal, or any other rigid or semi-rigid material.

In further aspects, the present invention relates to an insert for a catheter connector for use during packaging, shipping, and handling of the catheter connector. The insert includes a rod-shaped member configured to fit within the catheter connector. The catheter connector has a body with a first half axially aligned with a second half. The first half is rotatable relative to the second half between an open position and a closed position. Thus, the rod-shaped member is configured to fit within the first and second halves when the catheter connector is in the open position such that the insert maintains the catheter connector in the open position during packaging, shipping, and handling of the catheter connector. It should be understood that the insert may also include any of the additional features as described herein.

In still additional aspects, the present invention relates to an insert for a catheter connector for use during packaging, shipping, and handling of the catheter connector. The insert includes a housing configured to fit at least partially around an exterior surface of the catheter connector. Further, the catheter connector has a body with a first half axially aligned with a second half. The first half is rotatable relative to the second half between an open position and a closed position. The housing includes a hollow interior having a shape that corresponds to an exterior shape of the catheter connector in the open position. Thus, at least a portion of the catheter connector is configured to fit within the housing of the insert when in the open position such the insert maintains the catheter connector in the open position during packaging, shipping, and handling of the catheter connector. It should be understood that the insert may also include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 1 illustrates a perspective view of one embodiment of a catheter connector of conventional construction in a closed position;

FIG. 2 illustrates a perspective view of the catheter connector of FIG. 1 in an open position;

FIG. 3 illustrates a perspective view of the catheter connector of FIG. 1 separated into two halves to illustrate various internal components of the connector;

FIG. 4 illustrates a perspective view of one embodiment of an insert for a catheter connector in accordance with aspects of the invention;

FIG. 5 illustrates a perspective view of one embodiment of the insert of FIG. 4 configured with a catheter connector in accordance with aspects of the invention;

FIG. 6 illustrates a perspective view of another embodiment of an insert for a catheter connector in accordance with aspects of the invention; and FIG. 7 illustrates a perspective view of one embodiment of the insert of FIG. 6 configured with a catheter connector in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to a catheter connector assembly having an insert that maintains a catheter connector in an open position during packaging, shipping, and handling. More specifically, the assembly includes a catheter connector, e.g. a Stingray™ connector, having a body with a first half axially aligned with a second half. The first half is rotatable relative to the second half between an open position and a closed position. The first half defines a distal end of the body and the second half defines a proximal end of the body. A proximal end port is configured with the proximal end of the second half for mating communication with a fluid delivery device. The insert is configured with the body when the body is in the open position such that the insert maintains the catheter connector in the open position during packaging, shipping, and handling of the catheter connector.

The present disclosure has many advantages not present in the prior art. For example, the insert provides a simple, easy-to-use component that maintains a catheter connector in an open position during packaging, shipping, and handling. As such, the internal components of the catheter connector are not compromised before being used for a patient. In addition, the insert is relatively inexpensive to manufacture and can be used in conjunction with many catheter connectors, such as the Stingray™ connector as described herein.

Referring now to the drawings, FIGS. 1-3 illustrate various views of one embodiment of a catheter connector 10 that can be used in conjunction with the insert of the present disclosure. As shown, the catheter connector 10 includes a body 16 having a proximal end 18 and distal end 20. The body 16 has a first half 22 axially aligned with a second half 24. The first half 22 defines a distal end 20 of the body 16 and the second half 24 defines a proximal end 18 of the body 16. A proximal end port 14 is configured with the proximal end 18 of the second half 24 for mating communication with a fluid delivery device (not shown). As mentioned, the fluid delivery device may be any suitable device known in the art, such as a pump, reservoir, syringe, or the like. Further, the proximal end port 14 may have any conventional configuration, such as a Luer-lock fitting.

The first half 22 is rotatable relative to the second half 24 between an open position (FIG. 2) and a closed position (FIG. 1). More specifically, as shown in FIG. 3, the first half 22 may include a bushing 25 extending from an interior surface 23 thereof. In certain embodiments, an elastomeric tube 27 may be configured within the bushing 25. Further, the second half 24 may include a corresponding cavity 29 configured to receive the bushing 25 therein. Thus, the axially aligned halves 22, 24 of the connector 10 are configured to twist to the open position (FIG. 2) to allow insertion of a catheter through a catheter insertion hole 15 in the first half 22, and subsequently twist to a closed position (FIG. 1) with an audible and tactile click that indicates complete engagement with the catheter. More specifically, the elastomeric tube 27 within the bushing 25 compresses and grips the catheter when the connector 10 is in the closed position (FIG. 1). In certain embodiments, the open position is defined by the first half 22 being rotated relative to the second half 24 at an approximately 45-degree angle. In further embodiments, the first half 22 may be rotated to any suitable angle relative to the second half 24.

Referring to FIG. 4, one embodiment of an insert 26 configured to maintain the catheter connector 10 of FIGS.

1-3 in an open position during packaging, shipping, and handling is illustrated. As shown, the insert 26 includes a rod-shaped member 28 and a tab member 30. The rod-shaped member 28 has proximal end 31 and a distal end 33. Further, the rod-shaped member 28 is shaped such that the proximal end 31 can be inserted through the catheter connector 10 when the connector 10 is in an open position. For example, in one embodiment, the rod-shaped member 28 may have a substantially circular cross-section so as to correspond with the cross-sectional shape of a catheter. Thus, as shown in FIG. 5, a portion of the rod-shaped member 28 may be inserted through the first and second halves 22, 24 of the catheter connector 10 through the catheter insertion hole 15 so as to maintain the connector 10 in an open position. In addition, as shown, the tab member 30 is configured with the distal end 33 of the rod-shaped member 28 such that the tab member 30 extends outside of the distal end 20 of the catheter connector 10 when the rod-shaped member 28 is inserted within the first and second halves 22, 24 of the connector 10. Thus, the tab member 30 is configured to assist a user with removing the insert 26 from within the catheter connector 10 (e.g. after the connector 10 has been shipping and is ready to be used with a catheter that is inserted into a patient).

Referring now to FIG. 6, another embodiment of an insert 46 configured to maintain the catheter connector 10 of FIGS. 1-3 in an open position during packaging, shipping, and handling is illustrated. As shown, the insert 46 is configured to fit at least partially around an exterior surface of the body 16 of the connector 10 when the body 16 is in the open position such that the insert 46 maintains the catheter connector 10 in the open position. For instance, as shown in the illustrated embodiment, the insert 46 includes a housing 32 having a hollow interior 34 that is shaped so as to correspond to an exterior shape of the catheter connector 10 when the connector 10 is in the open position. More specifically, in certain embodiments, the housing 32 includes a plurality of compartments 38 that correspond to the rotated first and second halves 22, 24 in the open position. Thus, as shown in FIG. 7, at least a portion of the catheter connector 10 is configured to fit within the housing 32 when the connector 10 is in the open position such that the insert 46 maintains the catheter connector 10 in the open position during packaging, shipping, and handling.

Still referring to FIGS. 6 and 7, the insert 46 may also include one or more locking features 36 configured to secure the insert 46 at least partially around the exterior surface of the body 16 of the connector 10. For example, in certain embodiments, the locking features 36 may include any one of or combination of the following: molded snaps, add-on grips, ridges, protrusions, an adhesive, or similar.

It should also be understood that the inserts 26, 46 as described herein may be constructed of any suitable material. For example, in certain embodiments, the inserts 26, 46 may be constructed of a rigid or semi-rigid material, such as a metal or a hard plastic. More specifically, the inserts 26, 46 may be constructed of polypropylene, polycarbonate, polyurethane, polyester, epoxy resins, phenolic resins, polyvinyl chloride (PVC), or any other suitable polymer material. In addition, the inserts 26, 46 may be constructed of aluminum, copper, stainless steel, or any other suitable metal. In some embodiments, the inserts 26, 46 may also be constructed of a flexible or semi-flexible material, such as a rubber material, a polymeric material, a silicone material, an elastomeric material, or similar. More specifically, in various embodiments, the inserts 26, 46 may be constructed of polyisoprene, polyurethane, styrene butadiene, and/or any other suitable flexible material.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A catheter connector assembly, comprising:
    a catheter connector comprising a body having a first half axially aligned with a second half, said first half rotatable relative to said second half between an open position and a closed position, said first half defining a distal end of said body and said second half defining a proximal end of said body;
    a proximal end port configured with said proximal end of said body for mating communication with a fluid delivery device; and
    an insert comprising an axially-extending rod-shaped member fitting within said first and second halves of said body when said body is in said open position such that said insert maintains said catheter connector in said open position during packaging, shipping, and handling of the catheter connector, the rod-shaped member having a longitudinal axis extending along a longitudinal axis of the first and second halves of said body.

2. The catheter connector assembly of claim 1, wherein said insert further comprises a tab member at a distal end of said rod-shaped member, said tab member extending outside of said catheter connector when said rod-shaped member is inserted within said first and second halves of said body, said tab member configured to assist a user with removing said insert from said catheter connector.

3. The catheter connector assembly of claim 1, wherein said open position comprises said first half being rotated relative to said second half at an approximately 45-degree angle.

4. The catheter connector assembly of claim 1, wherein said insert is constructed of a rigid material.

5. The catheter connector assembly of claim 4, wherein said rigid material comprises at least one of or a combination of the following: a plastic material, polycarbonate, polypropylene, polyurethane, polyester, epoxy resins, phenolic resins, polyvinyl chloride (PVC), or metal.

* * * * *